United States Patent
Gruzins et al.

(10) Patent No.: US 6,716,913 B1
(45) Date of Patent: Apr. 6, 2004

(54) POLYOLS CONTAINING GRAFTED CARBOXYL GROUPS AND METHOD OF MAKING SAME

(75) Inventors: Indulis Gruzins, Louisville, KY (US); Donald Farrell McElheney, Louisville, KY (US); Robert C. Hire, Dayville, CT (US); Jerry Douglas Necessary, Elizabethtown, KY (US)

(73) Assignee: Arch Chemicals, Inc., Norwalk, CT (US)

( * ) Notice: Subject to any disclaimer, the term of this patent is extended or adjusted under 35 U.S.C. 154(b) by 188 days.

(21) Appl. No.: 09/723,263

(22) Filed: Nov. 27, 2000

(51) Int. Cl.⁷ .................. C08K 83/00; C08L 75/00; C08G 63/02; C08G 63/66; C08G 63/00
(52) U.S. Cl. .................. 524/840; 524/591; 528/272; 528/300; 528/307
(58) Field of Search .................. 524/840, 591, 524/834; 528/272, 300, 307

(56) References Cited

U.S. PATENT DOCUMENTS

| | | | |
|---|---|---|---|
| 4,207,227 A | 6/1980 | von Bonin | 260/40 TN |
| 4,250,077 A | 2/1981 | von Bonin et al. | 260/37 N |
| 4,365,024 A | 12/1982 | Frentzel | 521/114 |
| 4,460,738 A | 7/1984 | Frentzel et al. | 524/591 |
| 4,521,615 A | 6/1985 | Frentzel | 560/198 |
| 4,533,485 A | 8/1985 | O'Connor et al. | 252/156 |
| 5,242,954 A | 9/1993 | Hire et al. | 521/157 |
| 5,250,582 A | 10/1993 | Hire et al. | 521/157 |
| 5,863,980 A | 1/1999 | Choi et al. | 524/591 |
| 5,880,250 A | 3/1999 | Housel et al. | 528/272 |
| 6,103,822 A * | 8/2000 | Housel et al. | 524/840 |

* cited by examiner

Primary Examiner—Alan L. Rotman
Assistant Examiner—Taylor V Oh
(74) Attorney, Agent, or Firm—Dale Lynn Carlson; Todd E. Garabedian; Wiggin & Dana LLP

(57) ABSTRACT

The present invention is directed to carboxyl-containing monomers for use in preparing a polyurethane polymers, the carboxyl-containing monomers being the reaction product of a low molecular weight polyol compound and an acid anhydride in the presence of 5–500 ppm phosphoric acid, the carboxyl-containing monomer having a viscosity in the range of 3,000 to 100,000 centipoise, and having oligomer content of less than about 30 mg KOH/g. The present invention is also directed to methods of making the above carboxyl-containing monomers, as well as prepolymers and urethane polymers containing the above carboxyl-containing monomers.

19 Claims, No Drawings

POLYOLS CONTAINING GRAFTED CARBOXYL GROUPS AND METHOD OF MAKING SAME

BACKGROUND OF THE INVENTION

1. Field of the Invention

The present invention relates to monomers for use in the synthesis of polyurethanes, and more particularly to carboxyl-containing monomers made from a low molecular weight polyol compound and an acid anhydride, and in the presence of 5–500 ppm phosphoric acid.

2. Description of the Related Art

It is well known that polyurethanes are generally manufactured by reacting a polyisocyanate and a polyol. The produced polyurethane may have unique chemical and/or mechanical properties depending on the reacting conditions, as well as other additives such as catalysts, solvents, surfactants, blowing agents, fillers, and the like. The polyols used in manufacturing polyurethanes are typically low molecular weight poly-hydroxyl-containing polymers, such as those containing polyethers, polyesters, polyacrylics, polycarbonates, and the like. These polyols are generally provided with at least two hydroxyl groups so that they can be easily incorporated into a lengthening polymer in an ordered fashion.

Due to environmental and toxicity concerns, water-based polyurethanes and aqueous dispersions of polyurethanes are becoming the materials of choice for many applications, including aqueous applications. However, in many instances, the components of the polyurethane product are not easily soluble in water. To overcome this problem, it is known to introduce ionizable groups into the monomers prior to their condensation into the final polyurethane polymer. These ionizable groups are thought to aid in the solubilization of the polymer and thus produce a uniform aqueous dispersion of the final polyurethane mixture.

The reaction of succinic anhydride with triols or tetrols has been described generally in U.S. Pat. No. 5,863,980 to Kuen-Bae Choi. According to the disclosure, acid groups are introduced in the main chain in the absence of catalysts, including acid catalysts. In order to perform reaction between succinic anhydride and polyol, high reaction temperature was used and resulted in highly viscous polyols. When such highly viscous polyol was reacted with diisocyanate, a viscous prepolymer was obtained.

U.S. Pat. No. 4,207,2267 to Wulf von Bovin discloses a process for preparation of stable suspensions of inorganic fillers in poly-hydroxyl compounds by grafting olefinically unsaturated carboxylic acid onto polyol. As an example, acrylic acid and peroxide type initiators are used for this process.

U.S. Pat. No. 4,250,077 to Wulf von Bovin et al. discloses a suspension which is stable and contains inorganic filler and a graft polymer which was produced by free radical polymerization of olefinically unsaturated carboxylic acid.

U.S. Pat. No. 4,460,738 to Frentzel et al. discloses a process for grafting carboxyl groups to mono and polyether polyols by reacting maleic acid, fumaric acid, itaconic acid or their mixtures with polyether polyols in presence of peroxy-type free radical initiator.

U.S. Pat. No. 4,521,615 to Frentzel et al. discloses a process for grafting carboxyl groups to mono and polyether polyol by reacting maleic acid, fumaric acid or their mixtures with short chain polyether polyols in presence of peroxy-type free radical initiator.

U.S. Pat. No. 5,990,250 to Housel et al. discloses a process for incorporating carboxyl groups into main polyester chain by reacting polyether or polyester polyol with aliphatic dianhydride.

U.S. Pat. Nos. 5,242,954 and 5,250,582 to Hire et al. disclose a process for making cellular and microcellular polyurethane foams using a carboxylic acid-grafted polyol.

A common result of introduction of a carboxyl group into the polyol component is undesirable side reactions between the carboxyl group and nearby hydroxyl groups. The side reactions markedly increases viscosity of the monomer mixture, and provides fewer usable monomers for incorporation into the final aqueous urethane dispersion. In addition, the reacted carboxyl group results in reduced hydrophilicity of the final urethane dispersion.

Accordingly, there is a need in the art for water-soluble monomers to be incorporated into a urethane dispersion that possesses low viscosity, and does not undergo undesirable side reactions. The present invention is believed to be an answer to that need.

SUMMARY OF THE INVENTION

In one aspect, the present invention is directed to carboxyl-containing monomers for use in preparing a polyurethane polymer, the carboxyl-containing monomer being the reaction product of a low molecular weight polyol compound and an acid anhydride in the presence of 5–500 ppm phosphoric acid, the carboxyl-containing monomer having a viscosity in the range of about 3,000–100,000 centipoise, and having free oligomer content in the range of about 2–30 mg KOH/g.

In another aspect, the present invention is directed to a method of preparing a carboxyl-containing monomer for use in preparation of a polyurethane polymer, comprising the step of combining a low molecular weight polyol compound and an acid anhydride in the presence of 5–500 ppm phosphoric acid to produce the carboxyl-containing monomer, the carboxyl-containing monomer having a viscosity in the range of about 3,000 to about 100,000 cps and having a free oligomer content in the range of about 2 to about 30 mg KOH/g.

In another aspect, the present invention is directed to a prepolymer for use in preparing a polurethane polymer, the prepolymer being the reaction product of (1) the carboxyl-containing monomer described above, and (2) a polyisocyanate compound, the prepolymer having a viscosity in the range of about 3,000 to about 100,000 cps.

In another aspect, the present invention is directed to a method of preparing a prepolymer for use in preparation of a polyurethane polymer, comprising the step of combining the prepolymer described above with a polyisocyanate compound to produce the prepolymer, the prepolymer having a viscosity in the range of about 3,000 to about 100,000 cps.

In another aspect, the present invention is directed to a water-borne polyurethane polymer, the water-borne polyurethane polymer being the reaction product of (1) the prepolymer of described above, and (2) an amine compound.

These and other aspects will become apparent upon reading the following detailed description of the invention.

DETAILED DESCRIPTION OF THE INVENTION

It has been surprisingly found, in accordance with the present invention, that a carboxyl-containing monomer being the reaction product of a low molecular weight polyol compound and an acid anhydride, and made in the presence of phosphoric acid, results in a chemical monomer that is very beneficial for making waterborne polyurethane dispersions. The present inventors have unexpectedly discovered that phosphoric acid is very efficient in catalyzing polyol-anhydride addition reactions with anhydride ring opening mechanism, while exhibiting little or no acceleration of acid and polyol condensation side reactions.

In contrast to the prior art where the hydroxyl groups of polyol are reacted with polyisocyanate to produce polyurethane prepolymer, the monomer made according to the present invention possesses an polar center (by virtue of the grafted carboxyl function) that is thought to stabilize and solvate waterborne polyurethane emulsions when polyurethane prepolymer is dispersed in a water or alkaline-water solution. In addition, the presence of phosphoric acid in the reaction medium is thought to maintain the grafted carboxyl group in a protonated state and thus prevent it from participating in undesirable side reactions which lead to a high viscosity product that has limited usefulness.

The present invention provides a process for "grafting" carboxyl groups to polyol monomers, and the low-viscosity carboxyl-containing polyol monomers made by the process. The term "grafting" refers to addition of one molecule onto another molecule by means of a chemical reaction. The process of the present invention generally consists of reacting a polyol monomer, preferably containing three hydroxyl groups per molecule, with an organic acid anhydride under conditions such that an organic acid group is grafted to the polyol monomer. Because the polyol monomer is preferably selected to have three hydroxyl groups per molecule and is reacted with only one molecule of anhydride, the resulting carboxyl-containing monomer possesses two free hydroxyl groups per molecule and one carboxyl group grafted to the polyol. As indicated above, the two free hydroxyl groups of the carboxyl-containing monomer are used in subsequent reactions that form the ultimate polyurethane, while the carboxyl group aids in hydration of the polyurethane dispersion and prevents generation of highly viscous, unwanted side reactions and undesirable by-products.

As defined herein, the term "polyol" refers to compounds having between two and four free hydroxyl (—OH) groups per molecule, and preferably three hydroxyl groups. As defined herein, the phrase "low molecular weight polyol" refers to those polyols having a molecular weight less than 8,000, more preferably less than 2,000, and most preferably less than 500. The phrase "carboxyl-containing monomer" refers to a polyol having a carboxyl group added to one of the hydroxyl groups of the polyol.

As indicated above, in one aspect, the present invention is directed to a carboxyl-containing monomer for use in preparing a polyurethane polymer. The carboxyl-containing monomer is the reaction product of a low molecular weight polyol compound and an acid anhydride, and the resulting carboxyl-containing monomer has a viscosity in the range of 3,000–100,000 centipoise (cps) and has oligomer content in the range of 2–30 mg KOH/g. Each of these components are discussed in more detail below.

Examples of polyols that are useful in the present invention include low molecular weight polyols having from two to four hydroxyl groups. Preferably, the polyol contains three free hydroxyl groups (hereinafter termed "triol"). Triols suitable for use in the present invention are generally based on the structure of glycerol, trimethylolpropane, trimethylolethane, and the like. Preferred triols include Poly-G 76-635 (a polyether triol of molecular weight 265, available from Arch Chemicals, Inc..) and Poly-G 35-610 (a polyether triol of molecular weight 275), and their mixtures with trimethylolpropane or pure trimethylolpropane. Alternatively, polyalkylene polyether polyols produced by the poly-addition of any of the mentioned above triols and an alkylene oxide such as ethylene oxide, propylene oxide, butylene oxide, epoxybutene, and the like, may also be used. These triols usually have molecular weight from less than 100 to about 6000.

Suitable acid anhydrides used in the present invention include any acid anhydride that results in the addition of a carboxyl group to the monomer molecule. Useful acid anhydrides include maleic anhydride, phthalic anhydride, succinic anhydride, glutaric anhydride, and mixtures thereof. A preferred acid anhydride is succinic anhydride.

The preparation of the carboxyl-containing monomer is generally accomplished by reacting the low molecular weight polyol compound with an acid anhydride in the presence of phosphoric acid. Generally, the polyol is heated with anhydride to about 80–105° C. in presence of about 5–500 ppm of orthophosphoric acid ($H_3PO_4$), more preferably from about 100–400 ppm orthophosphoric acid, and most preferably from about 250–350 ppm orthophosphoric acid. According to the present invention, addition of 5–500 ppm of orthophosphoric acid catalyzes the selective reaction between polyol and anhydride, and an acid group is "grafted" to the polyol molecule. Preferably, a triol is selected that has three hydroxyl groups per molecule, and each triol molecule is reacted with one molecule of anhydride to generate a product that has two hydroxyl groups per molecule and one carboxyl group grafted to the polyol.

The reaction is monitored by acid number, and as soon as theoretical acid number has been reached, the reaction is stopped. In order to dry the reaction product, a solvent capable of forming an azeotropic mixture with water is added. Later, the azeotropic mixture of solvent and water is removed by vacuum distillation.

Preferably, the carboxyl-containing monomers are liquid at room temperature because liquids are more easy to handle as compared to solids. A useful range of viscosities for the carboxyl-containing monomers is generally less than 100,000 cps at 25° C. Preferably, the viscosity of the carboxyl-containing monomers is from about 3,000 to about 100,000 cps, more preferably from about 3,000 to about 50,000 cps, and most preferably from about 3,000 to about 20,000 cps.

The viscosity of prepolymers made with carboxyl containing monomers is preferably less than 100,000 centipoise (cps) at 25° C. in order to obtain good water borne dispersions. A preferred range of viscosity is from about 3,000 to about 100,000 cps, more preferably from about 3,000 to about 50,000 cps, and most preferably from about 3,000 to about 20,000 cps. If viscosity of prepolymer is more than 100,000 cps, the prepolymer usually is too thick for high speed mixing and no good waterborne dispersion can be obtained.

In order to increase the shelf life of prepolymer products made from the carboxyl-containing monomers, it is desirable that the carboxyl-containing monomers made as described above contain minimal amounts of oligomers. As defined herein, oligomers are molecules which result from the reaction of the grafted carboxyl function with another hydroxyl function, which can lead to oligomerization of the monomer products. Oligomers are undesirable due to their propensity to cause increased viscosity of the monomer product.

It has been found that the presence of oligomers above about 30 mg KOH/g (as analyzed below) results in undesirable gelling of the prepolymer product. Preferably, the carboxyl-containing monomers have less than 30 mg KOH/g oligomers, preferably between 2 and 30 mg KOH/g oligomers, more preferably between 2 and 20 mg KOH/g oligomers, and most preferably between about 2 and 15 mg KOH/g oligomers. Oligomer content in the carboxyl-containing monomer can be measured by calculating the difference between theoretical acid number and acid number determined by chemical analysis as known in the art.

Briefly, acid number is determined using 1–2 grams of sample. 100 ml of isopropyl alcohol and 50 ml water is added to the sample, and stirred until the sample is completely dissolved. Approximately 15 drops of 1% phenolphtalein solution is added, and the sample solution is titrated with 0.5 N potassium hydroxide (or 0.5 N sodium hydroxide) until a light pink color appears. Oligomer content in the carboxyl-containing monomer can be measured by calculating the difference between theoretical acid number and acid number determined by chemical analysis (expressed as mg KOH/g sample). This difference in mg KOH/g is then correlated to oligomeric ester units per gram of monomer.

As indicated above, the carboxyl-containing monomers prepared above may be used in the production of a "prepolymer". In general, the prepolymer is made by combining the carboxyl-containing monomers prepared above with a polyisocyanate compound. Organic polyisocyanates useful as reactants in the production of the prepolymer include any aromatic, cycloaliphatic and aliphatic diisocyanates and higher polyisocyanates. Diisocyanates are the preferred class of polyisocyanates. Suitable aliphatic diisocyanates include hexamethylene diisocyanate, 4,4'-dicyclohexylmethane diisocyanate; isophorone diisocyanate;1,4'-tetramethylene diisocyanate; and 1,10-decamethylene disiocyanate and 1,12-dodecamethylene diisocyanate. Suitable aromatic diisocyanates include toluene-2,4- or 2,6-diisocyanate; 1,5-naphthalene diisocyanates; 4-methoxy-1,3-phenylene diisocyanate; 4-chloro-1,3-phenylene diisocyanate; 2,4'-diisocyanatodiphenyl ether; 5,6-dimethyl-1,3-phenylate diisocyanate; 2,4-diemthyl-1,3-phenylene diisocyanate; 4,4'diisocyanatodiphenylether; benzidene diisocyanate, 4,4'-diisocyanataodibenzyl; methylene-bis(4-phenylisocyanate); and 1,3-phenylene diisocyanate. Particularly useful polyisocyanates for use in preparing the polyurethane prepolymers include toluene diisocyanate, 4,4'-diphenylmethane diisocyanate, 2,4'-diphenylmethane diisocyanate, hexamethylene diisocyanate, isophorone diisocyanate, 4,4'-dicyclohexyl-methane diisocyanate, 1,12-dodecanediisocyanate, 2,4,4-trimethylhexamethylene diisocyanate, xylylene diisocyanate, tetramethyl-xylylene diisocyanate and other polyisocyanates such as polymethylene polyphenyl isocyanate and isocyanate prepolymers having at least two isocyanate groups which are produced by reacting an isocyanate with a polyhydroxyl compound such as polyoxyalkylene polyol or polyester polyol or mixtures thereof.

The reaction in which hydroxyl groups are reacted with isocyanate groups and polyurethane prepolymer is produced is usually performed at 50–100° C. for 1–5 hours under an inert atmosphere such as nitrogen gas and at atmospheric pressure. Preferably the reaction is performed at 70–90° C. for 2–3 hours.

The ratio of isocyanate to carboxyl-containing polyol is such as to have the desired amount of grafted carboxyl groups per molecule of polyurethane prepolymer. Usually, the carboxyl-containing monomer is added to result in an acid number for the prepolymer of 10–30 mg KOH/g. The preferred procedure for producing the prepolymer is to react the selected polyisocyanate with regular polyether or polyester polyol for 1–2 hours at 80–90° C., and then add carboxyl-containing monomers until the theoretical isocyanate group content has been reached. If desired, catalysts such as dibutyltin dilaurate, stannous octoate, or amine-type catalysts like triethylamine or triethylene diamine, may be used to assist prepolymer formation. The prepolymer composition may also include solvents such as methylethylketone, methylpyrrolidone, and the like Because carboxyl groups are grafted to the polyol molecule, the resulting main polyurethane chain is linear with carboxyl groups as side pendants. This structure is ideal for obtaining good water-borne dispersions. The chemical structure of an exemplary prepolymer made from 1 mole of 1000 molecular weight propylene oxide based diol (Poly-G 20-112 from Arch Chemicals, Inc., Norwalk, Conn.), three moles of 4,4'dicyclohexylmethane diisocyanate, and one mole of trimethylolpropane with succinic anhydride grafted to a side chain is as follows:

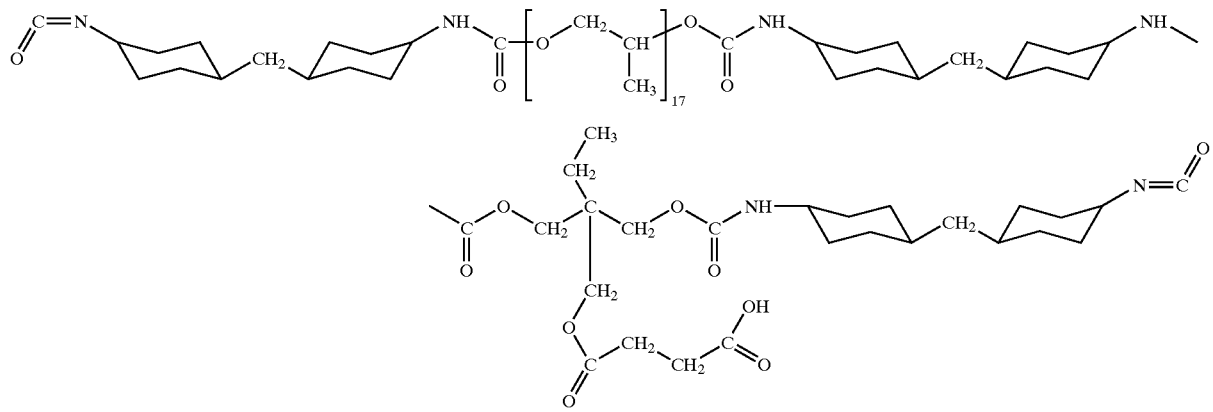

This prepolymer is easy to disperse in water by converting side pendant carboxyl groups into salt groups and then reacting free NCO groups with diamine to obtain a high molecular weight urethane dispersion in water. Because, according to the present invention, there is one carboxyl group grafted to each triol molecule, the resulting prepolymer has low viscosity, low oligomer content, and is very easy to disperse in water. The dispersion process proceeds easily and water-borne dispersions may be prepared without the use of high shear/high speed mixers.

The prepolymer described above, may be combined with an amine compound to extend the prepolymer and further dispers the polymer in water. Suitable amines for dispersing prepolymer in water and chain extending the prepolymer include triethylamine, tripropylamine, ethylene diamine, n-butylamine, diethylamine, trimethylamine, monoethanol amine, dimethylethanolamine, aminoalcohols, hydrazine, hexamethylene diamine, isophorone diamine, cyclohexane diamine, dimethylcyclohexylamine, tris(3-aminopropyl) amine, 2-methylpentamethylenediamine, 1,12-dodecanediamine and combinations thereof.

The chain extension reaction occurs when free isocyanate groups of water dispersed prepolymer react with amino groups and is described in the art. The reaction between isocyanate groups and amine groups is very fast and chain extension step can be carried out in water.

It may be desirable to add other conventional additives such as blowing agents, thickening agents, pH adjusters, monoisocyanates and the like to the composition of the invention. Furthermore, fillers, plasticizers, pigments, and the like may be utilized as desired. It may be also desirable to add other polyurethane prepolymers made from modified or unmodified polyether polyols or polyester polyols or the like.

The following examples are intended to illustrate, but in no way limit the scope of the present invention. All parts and percentages are by weight and all temperatures are in degrees Celsius unless explicitly stated otherwise.

EXAMPLES

Example 1

Grafting Carboxyl Groups to Polyether Triol

To a flask equipped with a thermometer, stirrer and reflux condenser were added 1696 grams of polyol Poly-G 76-635 (polyether triol with OH number 635 made by Arch Chemicals, Norwalk, Conn.) and 0.45 grams of 85% ortho phosphoric acid (Aldrich Chemical, St. Louis, Mo.). The mixture was stirred at room temperature for 30 minutes and then 645.3 grams of succinic anhydride were added (Aldrich). With agitation the working temperature was increased to 98° C. and the mixture heated for 2 hours. After 2 hours, a sample for acid number was taken and compared to a theoretical value. With an acid number higher than theoretical heating was continued and then sampled every half hour till an acid number was 2 to 5 units from theoretical. When the acid number was in the desired range, 58.4 grams isopropanol were added. The equipment was then switched to vacuum distillation with stirring while heating for 90 minutes at 85° C. and vacuum of 14 mm Hg.

For comparison purposes, an experiment with the same polyol and succinic acid anhydride ratio except that this time no phosphoric acid was added and reaction was performed according to the procedure described in U.S. Pat. No. 5,863,980. The resulting polyols are compared in Table 1.

TABLE 1

|  | Experiment 1 (Prior Art) | Experiment 2 (Present Process) |
| --- | --- | --- |
| Triol Used | Polyether Polyol 76-635 from Arch Chemical | Polyether Polyol 76-635 from Arch Chemical |
| $H_3PO_4$, ppm | 0 | 227 |
| Temp. (° C.) | 135 | 98 |
| Theoretical Acid | 155.2 | 155.2 |
| Found Acid | 120 | 153 |
| Oligoester, mgKO H/g | 35.2 | 2.2 |
| Oligoester/Acid | 0.2933 | 0.014 |
| OH # | 289 | 321 |
| pH | 3.4 | 3.3 |
| Viscosity at 25 C. | 16720 | 8800 |
| MW by GPC | 500 | 408 |
| Calculated MW | 361 | 361 |
| MW Difference | 139 | 47 |

The data in Table 1 show that the polyol obtained according to the prior art was 1.9 times more viscous and contained 16 times more oligoester units. Also there was significant difference between the molecular weight determined by GPC for this polyol and that calculated from the formula. Polyol with grafted carboxyl groups made according to this invention was less viscous, contained only few oligoester groups and the molecular weight determined by GPC was close to the theoretical molecular weight calculated.

Polyols obtained in experiments 1 and 2 above were reacted with 2000 molecular weight polyether diol Poly-G 20-56 (made by Arch Chemicals) and 4,4'-dicyclohexylmethane diisocyanate (Desmodur W made by Bayer) to produce prepolymers. Table 2 compares properties of the prepolymer obtained in this process to polyol obtained according to U.S. Pat. No. 5,863,980 ("Prior Art").

TABLE 2

|  | Experiment 3 (Prior Art) | Experiment 4 (Present Process) |
| --- | --- | --- |
| Raw Materials Used | Polyol of Exp. 1, Polyether diol, Poly-G 20-56, Desmodur W | Polyol of Exp. 2, Polyether diol, Poly-G 20-56, Desmodur W |
| NCO/OH ratio | 1.3 | 1.3 |
| Acid # of Prepolymer | 30.8 | 31.3 |
| NCO % Theoretical | 2.06 | 2.00 |
| NCO % After Reaction | 2.19 | 2.14 |
| Viscosity at 25 C. (measured after reaction) | 416,000 | 11,160 |
| NCO % After 16 Hours | gel | 2.13 |
| Viscosity at 25 C. After 16 Hours | gel | 21,520 |

As can be seen in Table 2, prepolymer obtained from polyol made according to U.S. Pat. No. 5,863,980 was 37 times more viscous than prepolymer made with polyol containing grafted carboxyl groups and eventually gelled after 15 hours. Table 3 contains data on the results of grafting carboxyl groups according to the present invention to different triols.

TABLE 3

Grafting of carboxyl groups to triols

| Exp. No. | 2 (above) | 5 | 6 | 7 | 8 | 9 | 10 | 11 | 12 |
|---|---|---|---|---|---|---|---|---|---|
| Triol Used | Polyether Polyol 76-635 | Polyether Polyol 76-635 | Polyether Polyol 76-635 | Polyether Polyol 76-635 | TMP | TMP | TMP | TMP | Polyether Polyol 35-610 from Arch Chemicals |
| Phosphoric Acid ppm | 227 | 5 | 5 | 227 | 316 | 316 | 300 | 320 | 5 |
| Temp. C. | 98 | 100 | 100 | 98 | 100 | 100 | 80 | 103 | 80 |
| Isopropanol added % | 0 | 0 | 2.5 | 2.14 | 0 | 4.2 | 0 | 2.5 | 0 |
| Theoretical Acid # | 155.2 | 155.2 | 155.2 | 155.2 | 239.5 | 239.5 | 239.5 | 239.5 | 150.9 |
| Found Acid # | 153 | 150.7 | 146.7 | 149.3 | 224.5 | 219 | 227.5 | 213.4 | 147.8 |
| Oligoester, mgKOH/g | 2.2 | 4.5 | 8.5 | 5.9 | 15 | 20.5 | 12 | 26.1 | 3.1 |
| Oligoester/Acid | 0.014 | 0.030 | 0.058 | .0395 | 0.067 | 0.086 | 0.0527 | 0.1223 | 0.0209 |
| OH # | 321 | 322 | 311 | 316 | 449.7 | 451 | 455.3 | 439.7 | 300.7 |
| Water % | 0.2 | 0.3 | 0.05 | .05 | 0.6 | 0.31 | 0.41 | 0.41 | 0.24 |
| pH | 3.3 | 3.1 | 3.1 | 3.3 | 3.2 | 3.1 | 3.1 | 3.1 | 3.2 |
| Viscosity at 25 C. | 8800 | 11500 | 12600 | 8840 | 97200 | 108400 | 77600 | 90800 | 4265 |
| MW by GPC | 408 | 392 | 405 | 408 | 302 | 297 | 315 | 287 | 374 |
| Calculated MW | 361 | 361 | 361 | 361 | 234 | 234 | 234 | 234 | 371.9 |
| MW Difference | 47 | 31 | 44 | 47 | 68 | 63 | 81 | 53 | 2.1 |

In Table 3, TMP is trimethylolpropane.

Example 2

Grafting Carboxyl Groups to Trimethylolpropane

To a flask equipped with thermometer, stirrer and reflux condenser were added 1341.8 grams of trimetylolpropane (Aldrich). Without agitation the temperature was slowly increased to 95° C. to melt the trimethylolpropane. To the melted trimethylolpropane melted were added 0.753 grams of 85% ortho phosphoric acid (Aldrich) and 1000.7 grams of succinic anhydride (Aldrich). With agitation, the slurry was heated to and held at 100° C. until all solids were dissolved. As soon as there were no solids in the flask, it was sampled for acid number and compared to the theoretical value. With acid number higher than theoretical, heat was continued and sampled every 15 minutes till an acid number was 2 to 5 units from theoretical. When the acid number was in desired range 101.9 grams isopropanol were added, switched to a vacuum distillation setting and with stirring heated for 60 minutes at 80 C. and vacuum of 14 mm Hg.

Example 3

Preparation of Water-Borne Polyurethane Dispersion 38 grams of 4,4'-dicyclohexylmethane diisocyanate ("DESMODUR W" from by Bayer), 22.3 of polyether diol with molecular weight 425 (Poly-G 20-265 from Arch Chemicals), 0.008 grams of dibutyltin dilaurate (catalyst Dabco T-12 from Air Products), and 18.7 grams of methylethylketone were mixed and heated to 85° C. and maintained at that temperature for 1 hour. After 1 hour, 21 grams of polyol with grafted carboxyl groups was added. This polyol with grafted carboxyl groups was obtained by reacting 1 mol of Poly-G 76-635 with 1 mol of succinic anhydride as described in Example 1, and had an equivalent weight of 179.4 for each OH group, and an equivalent weight 381.6 for each carboxyl group. After adding the polyol with grafted carboxyl groups, heating was continued for 2 more hours at 85° C. The NCO content of the prepolymer was analyzed and found to be 3.08%. The warm prepolymer was mixed at a high speed and then a mixture of 5.56 grams of triethylamine and 100 grams of water were added and mixed for 5 minutes to insure complete dispersion. No heating was applied at this stage. Temperature in flask after adding triethylamine and water was 46–47° C. A solution of 2.09 grams of ethylenediamine in 56.7 grams water was added to the dispersion and agitation was continued for 1 hour. The resulting dispersion was an opalescent liquid which after drying produced film with the following physical properties: Sword Hardness: 49; Tensile Strength: 3720 psi; Elongation at break: 52%

Example 4

Preparation of Water-Borne Polyurethane Dispersion 30.3 grams of 4,4'-dicyclohexylmethane diisocyanate ("DESMODUR W" from Bayer), 33 grams of polyether diol with molecular weight 1000 (Poly-G 20-112 from Arch Chemicals), 0.021 grams of dibutyltin dilaurate (Dabco T-12 from Air Products), and 16.7 grams of methylethylketone were mixed, heated to 85° C. and maintained at this temperature for 1 hour. After 1 hour, 20 grams of polyol with grafted carboxyl groups was added. This polyol with grafted carboxyl groups was obtained by reacting 1 mol of Poly-G 76-635 with 1 mol of succinic anhydride as described in Example 1 and had an equivalent weight of 178.3 for each OH group and an equivalent weight of 375.7 for each carboxyl group. After adding the polyol with grafted carboxyl groups, heating was continued for 2 more hours at 85° C. The NCO content of the prepolymer was analyzed and found to be 2.05%. The warm prepolymer was mixed at a high speed, and then a mixture of 5.4 grams of triethylamine and 100 grams of water were added and mixed for 5 minutes to insure complete dispersion. No heating was applied at this stage. Temperature in flask after adding triethylamine and water was 46–47° C. A solution of 1.39 grams of ethylenediamine in 56.7 grams water was added to the dispersion and agitation was continued for 1 hour. The resulting dispersion was an opalescent liquid which after drying produced film with the following physical properties: Sword Hardness: 12; Tensile Strength: 1840 psi; Elongation at break: 465%; 100% modulus: 697 psi; Tear resistance: 189 p/in.

Example 5

Preparation of Water-Borne Polyurethane Dispersion 26.2 grams of 4,4'-dicyclohexylmethane diisocyanate (DESMODUR W from Bayer), 33 grams of polyether diol with molecular weight 2000 (Poly-G 20-56 from Arch Chemicals), 0.01 grams of dibutyltin dilaurate (Dabco T-12 from by Air Products), and 17.8 grams of methylethylketone were mixed and heated to 85° C. and maintained at that temperature for 1 hour. After 1 hour, 21 grams of polyol with grafted carboxyl groups was added. This polyol with grafted carboxyl groups was obtained by reacting 1 mol of Poly-G 76-635 with 1 mol of succinic anhydride as described in Example 1 and had an equivalent weight of 178.3 for each OH group and an equivalent weight of 375.7 for each carboxyl group. After adding polyol with the grafted carboxyl groups heating was continued for 2 more hours at 85° C. The NCO content of the prepolymer was analyzed and found to be 2.72%. The warm prepolymer was mixed at a high speed and then a mixture of 5.65 grams of triethylamine and 100 grams of water were added and mixed for 5 minutes to insure complete dispersion. No heating was applied at this stage. Temperature in flask after adding triethylamine and water was 46–47° C. A solution of 1.83 grams of ethylenediamine in 56.7 grams water was added to the dispersion and agitation was continued for 1 hour. The resulting dispersion was an opalescent liquid which after drying produced film with the following physical properties: Sword Hardness: 18; Tensile Strength: 1780 psi; Elongation at break: 510%; 100% modulus: 730 psi; Tear resistance: 254 p/in.

Example 6

Preparation of Water-Borne Polyurethane Dispersion 23.66 grams of 4,4'-dicyclohexylmethane diisocyanate (Desmodur W from Bayer), 39.7 grams of polyether diol with molecular weight 3000 (Poly-G 20-37 from Arch Chemicals), 0.020 grams of dibutyltin dilaurate (Dabco T-12 from Air Products), and 16.64 grams of methylethylketone were mixed and heated to 85° C. and maintained at that temperature for 1 hour. After 1 hour, 20 grams of polyol with grafted carboxyl groups was added. This polyol with grafted carboxyl groups was obtained by reacting 1 mol of Poly-G 76-635 with 1 mol of succinic anhydride as described in Example 1 and had an equivalent weight of 177.53 for each OH group and an equivalent weight of 374 for each carboxyl group. After adding polyol with grafted carboxyl groups heating was continued for 2 more hours at 85° C. The NCO content of the prepolymer was analyzed and found to be 2.51%. The warm prepolymer was mixed at a high speed and then a mixture of 5.4 grams of triethylamine and 100 grams of water were added and mixed for 5 minutes to insure complete dispersion. No heating was applied at this stage. Temperature in flask after adding triethylamine and water was 46–47° C. A solution of 1.7 grams of ethylenediamine in 56.7 grams water was added to the dispersion and agitation was continued for 1 hour. The resulting dispersion was an opalescent liquid which after drying produced film with the following physical properties: Sword Hardness: 22; Tensile Strength: 2000 psi; Elongation at break: 550%; 100% modulus: 1350 psi; Tear resistance: 328 p/in.

Example 7

Preparation of Water-Borne Polyurethane Dispersion 22.61 grams of 4,4'-dicyclohexylmethane diisocyanate ("DESMODUR W" from Bayer), 41 grams of polyether diol with molecular weight 4000 (Poly-G 20-28 from Arch Chemicals), 0.021 grams of dibutyltin dilaurate (Dabco T-12 from Air Products), and 16.4 grams of methylethylketone were mixed and heated to 85° C. and maintained at that temperature for 1 hour. After 1 hour, 20 grams of polyol with grafted carboxyl groups was added. This polyol with grafted carboxyl groups was obtained by reacting 1 mol of Poly-G 76-635 with 1 mol of succinic anhydride as described in Example 1 and had an equivalent weight of 178.3 for each OH group and an equivalent weight of 375.7 for each carboxyl group. After adding polyol with grafted carboxyl groups heating was continued for 2 more hours at 85° C. The NCO content of the prepolymer was analyzed and found to be 2.39%. The warm prepolymer was mixed at a high speed and then a mixture of 5.4 grams of triethylamine and 100 grams of water were added and mixed for 5 minutes to insure complete dispersion. No heating was applied at this stage. Temperature in flask after adding triethylamine and water was 46–47° C. A solution of 1.6 grams of ethylenediamine in 56.7 grams water was added to the dispersion and agitation was continued for 1 hour. The resulting dispersion was an opalescent liquid which after drying produced film with the following physical properties: Sword Hardness: 21; Tensile Strength: 1080 psi; Elongation at break: 180%; 100% modulus: 1000 psi; Tear resistance: 281 p/in.

Example 8

Preparation of Water-Borne Polyurethane Dispersion 61.3 grams of 4,4'-dicyclohexylmethane diisocyanate ("DESMODUR W" from Bayer), 65.2 grams of polyester diol with molecular weight 1000 (Rucoflex S101P-110 from by Ruco Polymer Corporation), 0.04 grams of dibutyltin dilaurate (Dabco T-12 from Air Products), and 33.5 grams of methylethylketone were mixed and heated to 85° C. and maintained at that temperature for 1 hour. After 1 hour 40 grams of polyol with grafted carboxyl groups was added. This polyol with grafted carboxyl groups was obtained by reacting 1 mol of Poly-G 76-635 with 1 mol of succinic anhydride as described in Example 1 and had an equivalent weight of 177.5 for each OH group and an equivalent weight of 374 for each carboxyl group. After adding polyol with grafted carboxyl groups heating was continued for 2 more hours at 85° C. The NCO content of prepolymer was analyzed and found to be 1.5%. The warm prepolymer was mixed at a high speed and then a mixture of 10.82 grams of triethylamine and 200 grams of water were added and mixed for 5 minutes to insure complete dispersion. No heating was applied at this stage. Temperature in flask after adding triethylamine and water was 46–47° C. A solution of 2.06 grams of ethylenediamine in 113.4 grams water was added to the dispersion and agitation was continued for 1 hour. The resulting dispersion was an opalescent liquid which after drying produced film with the following physical properties:

Sword Hardness: 18; Tensile Strength: 2155 psi; Elongation at break: 350%; 100% modulus: 1155 psi; Tear resistance: 274 p/in.

Example 9

Preparation of Water-Borne Polyurethane Dispersion 50.67 grams of 4,4'-dicyclohexylmethane diisocyanate ("DESMODUR W" from Bayer), 74 grams of polyester diol with molecular weight 2000 (Rucoflex S101-55 from Ruco Polymer Corporation), 0.04 grams of dibutyltin dilaurate (Dabco T-12 from Air Products), and 35.32 grams of methylethylketone were mixed and heated to 85° C. and maintained at that temperature for 1 hour. After 1 hour 40 grams of polyol with grafted carboxyl groups was added. This polyol with grafted carboxyl groups was obtained by reacting 1 mol of Poly-G 76-635 with 1 mol of succinic anhydride as described in Example 1 and had an equivalent weight of 177.5 for each OH group and an equivalent weight of 374 for each carboxyl group. After adding polyol with grafted carboxyl groups heating was continued for 3 more hours at 85° C. The NCO content of prepolymer was analyzed and found to be 2.06%. The warm prepolymer was mixed at a high speed and then a mixture of 10.82 grams of triethylamine and 200 grams of water were added and mixed for 5 minutes to insure complete dispersion. No heating was applied at this stage. Temperature in flask after adding triethylamine and water was 46–47° C. A solution of 2.7 grams of ethylenediamine in 113.4 grams water was added to the dispersion and agitation was continued for 1 hour. The resulting dispersion was an opalescent liquid which after drying produced film with the following physical properties: Sword Hardness: 28; Tensile Strength: 2870 psi; Elongation at break: 462%; 100% modulus: 1000 psi; Tear resistance: 377 p/i.

Example 10

Preparation of Water-Borne Polyurethane Dispersion 62.07 grams of 4,4'-dicyclohexylmethane diisocyanate ("DESMODUR W" from Bayer), 70 grams of polyether diol with molecular weight 1000 (Poly-G 20-112 from Arch Chemicals), 0.062 grams of dibutyltin dilaurate (Dabco T-12 from Air Products), 39.25 grams of methylethylketone was mixed and heated to 85° C. and maintained at that temperature for 1 hour. After 1 hour, 28.87 grams of polyol with grafted carboxyl groups was added. This polyol with grafted carboxyl groups was obtained by reacting 1 mol of trimethylolpropane with 1 mol of succinic anhydride as described in Example 2 and had equivalent weight 127.9 for each OH group and equivalent weight 268.4 for each carboxyl group. After adding polyol with grafted carboxyl groups heating was continued for 2 more hours at 85° C. The NCO content of prepolymer was analyzed and found to be 2.34%. Warm prepolymer was mixed fast and mixture of 10.82 grams of triethylamine and 200 grams of water was added and mixed for 5 minutes to insure complete dispersion. No heating to flask was applied at this stage. Temperature in flask after adding of triethylamine and water was 49–50° C. Solution of 3.16 grams of ethylenediamine in 163.4 grams of water was added to dispersion and agitation was continued for 2 hours. The resulting dispersion was opalescent liquid which after drying produced film with following physical properties: Sword Hardness: 29; Tensile Strength: 3960 psi; Elongation at break: 265%; 100% modulus: 2220 psi; Tear resistance: 265 p/in.

Example 11

Preparation of Water-Borne Polyurethane Dispersion 62.07 grams of 4,4'-dicyclohexylmethane diisocyanate ("DESMODUR W" from Bayer), 70 grams of polyether diol with molecular weight 1000 (Poly-G 20-112 from Arch Chemicals), 0.084 grams of triethylene diamine solution in dipropylene glycol (Dabco 33LV from Air Products), 39.25 grams of methylethylketone was mixed and heated to 85° C. and maintained at that temperature for 1 hour. After 1 hour 28.8 grams of polyol with grafted carboxyl groups was added. This polyol with grafted carboxyl groups was obtained by reacting 1 mol of trimethylolpropane with 1 mol of succinic anhydride as described in Example 2 and had equivalent weight 127.9 for each OH group and equivalent weight 268.4 for each carboxyl group. After adding polyol with grafted carboxyl groups heating was continued for 2 more hours at 85° C. The NCO content of prepolymer was analyzed and found to be 2.46%. Warm prepolymer was mixed fast and mixture of 10.82 grams of triethylamine and 200 grams of water was added and mixed for 5 minutes to insure complete dispersion. No heating to flask was applied at this stage. Temperature in flask after adding of triethylamine and water was 49–50° C. Solution of 3.3 grams of ethylenediamine in 113.4 grams of water was added to dispersion and agitation was continued for 2 hours. The resulting dispersion was opalescent liquid which after drying produced film with following physical properties: Sword Hardness: 28; Tensile Strength: 2590 psi; Elongation at break: 180%; 100% modulus: 2070 psi; Tear resistance: 385 p/in.

Example 12

Preparation of Water-Borne Polyurethane Dispersion 62.07 grams of 4,4'-dicyclohexylmethane diisocyanate ("DESMODUR W" from Bayer), 70 grams of polyether diol with molecular weight 1000 (Poly-G 20-112 from Arch Chemicals), 39.25 grams of methylethylketone was mixed and heated to 85° C. and maintained at that temperature for 1 hour. After 1 hour 0.235 grams of triethylamine and 28.8 grams of polyol with grafted carboxyl groups was added. This polyol with grafted carboxyl groups was obtained by reacting 1 mol of trimethylolpropane with 1 mol of succinic anhydride as described in Example 2 and had equivalent weight 127.9 for each OH group and equivalent weight 268.4 for each carboxyl group. After adding polyol with grafted carboxyl groups heating was continued for 1.5 more hours at 85° C. Additional 10.58 grams of triethylamine was added to flask and mixed for 1 hour at 85° C. Flask was cooled to 38° C. and 240 grams of water added with fast mixing. Theoretical NCO content of prepolymer was used to calculate ethylenediamine needed for chain extension. Solution of 3.1 grams of ethylenediamine in 113.4 grams of water was added to dispersion and agitation was continued for 2 hours. The resulting dispersion was opalescent liquid which after drying produced film with following physical properties: Sword Hardness: 30; Tensile Strength: 2260 psi; Elongation at break: 160%; 100% modulus: 2000 psi; Tear resistance: 290 p/in.

Example 13

Preparation of Water-Borne Polyurethane Dispersion 62.07 grams of 4,4'-dicyclohexylmethane diisocyanate ("DESMODUR W" from Bayer), 70 grams of polyether diol with molecular weight 1000 (Poly-G 20-112 made by Arch Chemicals) and 39.25 grams of methylethylketone was mixed and heated to 85° C. and maintained at that temperature for 1 hour. No urethane reaction catalyst was used for this experiment. After 1 hour 28.87 grams of polyol with grafted carboxyl groups was added. This polyol with grafted carboxyl groups was obtained by reacting 1 mol of trimethylolpropane with 1 mol of succinic anhydride as described in Example 2 and had equivalent weight 127.9 for each OH group and equivalent weight 268.4 for each carboxyl group. After adding polyol with grafted carboxyl groups heating was continued for 2 more hours at 85° C. Then NCO content of prepolymer was analyzed and found to be 2.44%. Warm prepolymer was mixed fast and mixture of 10.82 grams of triethylamine and 200 grams of water was added and mixed for 5 minutes to insure complete dispersion. No heating to flask was applied at this stage. Temperature in flask after adding of triethylamine and water was 49–50° C. 5.02 grams of 35% hydrazine solution and 113.4 grams of water were added to dispersion and agitation was continued for 2 hours. The resulting dispersion was opalescent liquid which after drying produced film with following physical properties: Sword Hardness: 25; Tensile Strength: 2210 psi; Elongation at break: 160%; 100% modulus: 1880 psi; Tear resistance: 250 p/in.

Example 14

Preparation of Water-Borne Polyurethane Dispersion 62.07 grams of 4,4'-dicyclohexylmethane diisocyanate ("DESMODUR W" from Bayer), 70 grams of polyether diol with molecular weight 1000 (Poly-G 20-112 from Arch Chemicals) and 39.25 grams of methylethylketone was mixed and heated to 85° C. and maintained at that temperature for 1 hour. No urethane reaction catalyst was used for this experiment. After 1 hour 28.87 grams of polyol with grafted carboxyl groups was added. This polyol with grafted carboxyl groups was obtained by reacting 1 mol of trimethylolpropane with 1 mol of succinic anhydride as described in Example 2 and had equivalent weight 127.9 for each OH group and equivalent weight 268.4 for each carboxyl group. After adding polyol with grafted carboxyl groups heating was continued for 4 more hours at 85° C. Then NCO content of prepolymer was analyzed and found to be 2.17%. Warm prepolymer was mixed fast and mixture of 10.82 grams of triethylamine and 200 grams of water was added and mixed for 5 minutes to insure complete dispersion. No heating to flask was applied at this stage. Temperature in flask after adding of triethylamine and water was 49–50° C. 5.68 grams of hexamethylene diamine and 134 grams of water were added to dispersion and agitation was continued for 2 hours. The resulting dispersion was opalescent liquid which after drying produced film with following physical properties: Sword Hardness: 27; Tensile Strength: 2500 psi; Elongation at break: 120%; 100% modulus: 2000 psi; Tear resistance: 225 p/in.

Example 15

Preparation of Water-Borne Polyurethane Dispersion 69.1 grams of 4,4'-dicyclohexylmethane diisocyanate ("DESMODUR W" from Bayer), 63.6 grams of polyether diol with molecular weight 1000 (Poly-G 20-112 made by Arch Chemicals), 0.088 grams of dibutyltin dilaurate (Dabco T-12 from Air Products), 39.35 grams of methylethylketone was mixed and heated to 85° C. and maintained at that temperature for 1 hour. After 1 hour 28.0 grams of polyol with grafted carboxyl groups was added. This polyol with grafted carboxyl groups was obtained by reacting 1 mol of trimethylolpropane with 1 mol of succinic anhydride as described in Example 2 and had equivalent weight 124.76 for each OH group and equivalent weight 249.9 for each carboxyl group. After adding polyol with grafted carboxyl groups heating was continued for 2 more hours at 85° C. The NCO content of prepolymer was analyzed and found to be 3.22%. Warm prepolymer was mixed fast and mixture of 11.33 grams of triethylamine and 200 grams of water was added and mixed for 5 minutes to insure complete dispersion. No heating to flask was applied at this stage. Temperature in flask after adding of triethylamine and water was 49–50° C. Solution of 4.36 grams of ethylenediamine in 113.4 grams of water was added to dispersion and agitation was continued for 2 hours. The resulting dispersion was opalescent liquid which after drying produced film with following physical properties: Sword Hardness: 44; Tensile Strength: 4000 psi; Elongation at break: 20%.

Example 16

Preparation of Water-Borne Polyurethane Dispersion 75.47 grams of 4,4'-dicyclohexylmethane diisocyanate ("DESMODUR W" from Bayer), 57.2 grams of polyether diol with molecular weight 1000 (Poly-G 20-112 from Arch Chemicals), 0.079 grams of dibutyltin dilaurate (Dabco T-12 from Air Products), 39.35 grams of methylethylketone was mixed and heated to 85° C. and maintained at that temperature for 1 hour. After 1 hour 28 grams of polyol with grafted carboxyl groups was added. This polyol with grafted carboxyl groups was obtained by reacting 1 mol of trimethylolpropane with 1 mol of succinic anhydride as described in Example 2 and had equivalent weight 124.76 for each OH group and equivalent weight 249.9 for each carboxyl group. After adding polyol with grafted carboxyl groups heating was continued for 2 more hours at 85° C. The NCO content of prepolymer was analyzed and found to be 4.02%. Warm prepolymer was mixed fast and mixture of 11.33 grams of triethylamine and 200 grams of water was added and mixed for 5 minutes to insure complete dispersion. No heating to flask was applied at this stage. Temperature in flask after adding of triethylamine and water was 49–50° C. Solution of 5.45 grams of ethylenediamine in 113.4 grams of water was added to dispersion and agitation was continued for 2 hours. The resulting dispersion was opalescent liquid which after drying produced film with following physical properties: Sword Hardness: 58; Sample was too brittle to perform tensile and tear tests.

Example 17

Preparation of Water-Borne Polyurethane Dispersion 62.24 grams of 4,4'-dicyclohexylmethane diisocyanate ("DESMODUR W" from Bayer), 70.5 grams of polyether diol with molecular weight 1000 (Poly-G 20-112 from Arch Chemicals), 0.084 grams of dibutyltin dilaurate (Dabco T-12 from Air Products), 39.25 grams of methylethylketone was mixed and heated to 85° C. and maintained at that temperature for 1 hour. After 1 hour 28.0 grams of polyol with grafted carboxyl groups was added. This polyol with grafted carboxyl groups was obtained by reacting 1 mol of trimethylolpropane with 1 mol of succinic anhydride as described in Example 2 and had equivalent weight 124.76 for each OH group and equivalent weight 249.9 for each carboxyl group. After adding polyol with grafted carboxyl groups heating was continued for 2 more hours at 85° C. The NCO content of prepolymer was analyzed and found to be 2.21%. Warm prepolymer was mixed fast and mixture of 11.33 grams of triethylamine and 300 grams of water was added and mixed for 5 minutes to insure complete dispersion. No heating to flask was applied at this stage. Temperature in flask after adding of triethylamine and water was 49–50° C. Solution of 8.43 grams of isophorone diamine in 200 grams of water was added to dispersion and agitation was continued for 2 hours. The resulting dispersion was opalescent liquid which after drying produced film with following physical properties: Sword Hardness: 36; Tensile Strength: 3600 psi; Elongation at break: 175%; 100% modulus: 2750 psi; Tear resistance: 450 p/in.

Example 18

Preparation of Water-Borne Polyurethane Dspersion 54.98 grams of isophorone diisocyanate ("LUXATE IM" from Loyondell Chemical Co.), 77.8 grams of polyether diol with molecular weight 1000 (Poly-G 20-112 made by Arch Chemicals), 0.061 grams of dibutyltin dilaurate (Dabco T-12 from Air Products), 39.25 grams of methylethylketone was mixed and heated to 85° C. and maintained at that temperature for 1 hour. After 1 hour 28.0 grams of polyol with grafted carboxyl groups was added. This polyol with grafted carboxyl groups was obtained by reacting 1 mol of trimethylolpropane with 1 mol of succinic anhydride as described in Example 2 and had equivalent weight 124.76 for each OH group and equivalent weight 256.6 for each carboxyl group. After adding polyol with grafted carboxyl groups heating was continued for 1.5 more hours at 85° C. The NCO content of prepolymer was analyzed and found to be 2.5%. Warm prepolymer was mixed fast and mixture of 11.04 grams of triethylamine and 300 grams of water was added and mixed for 5 minutes to insure complete dispersion. No heating to flask was applied at this stage. Temperature in flask after adding of triethylamine and water was 49–50° C. Solution of 3.38 grams of ethylenediamine in 200 grams of water was added to dispersion and agitation was continued for 2 hours. The resulting dispersion was opalescent liquid which after drying produced film with following physical properties: Sword Hardness: 18; Tensile Strength: 3010 psi; Elongation at break: 580%; 100% modulus: 586 psi; Tear resistance: 305 p/in.

Example 19

Preparation of Water-Borne Polyurethane Dispersion 54.98 grams of isophorone diisocyanate ("LUXATE IM" from Loyondell Chemical Co.), 77.8 grams of polyether diol with molecular weight 1000 (Poly-G 20-112 made by Arch Chemicals), 0.071 grams of dibutyltin dilaurate (Dabco T-12 from Air Products), 39.25 grams of methylethylketone was mixed and heated to 85° C. and maintained at that temperature for 1 hour. After 1 hour 28.0 grams of polyol with grafted carboxyl groups was added. This polyol with grafted carboxyl groups was obtained by reacting 1 mol of trimethylolpropane with 1 mol of succinic anhydride as described in Example 2 and had equivalent weight 124.33 for each OH group and equivalent weight 256.6 for each carboxyl group. After adding polyol with grafted carboxyl groups heating was continued for 1.5 more hours at 85° C. The NCO content of prepolymer was analyzed and found to be 2.43%. Warm prepolymer was mixed fast and mixture of 11.04 grams of triethylamine and 300 grams of water was added and mixed for 5 minutes to insure complete dispersion. No heating to flask was applied at this stage. Temperature in flask after adding of triethylamine and water was 49–50° C. Solution of 9.33 grams of isophorone diamine in 200 grams of water was added to dispersion and agitation was continued for 2 hours. The resulting dispersion was opalescent liquid which after drying produced film with following physical properties: Sword Hardness: 24; Tensile Strength: 3630 psi; Elongation at break: 340%; 100% modulus: 1550 psi; Tear resistance: 395 p/in.

Example 20

Preparation of Water-Borne Polyurethane Dispersion 54.98 grams of 2,4'-diphenylmethylene diisocyanate ("MONDUR ML" from Bayer), 72.9 grams of polyether diol with molecular weight 1000 (Poly-G 20-112 made by Arch Chemicals), 39.25 grams of methylethylketone was mixed and heated to 85° C. and maintained at that temperature for 1 hour. After 1 hour 28.0 grams of polyol with grafted carboxyl groups was added. This polyol with grafted carboxyl groups was obtained by reacting 1 mol of trimethylolpropane with 1 mol of succinic anhydride as described in Example 2 and had equivalent weight 124.33 for each OH group and equivalent weight 256.6 for each carboxyl group. After adding polyol with grafted carboxyl groups heating was continued for 1.5 more hours at 85° C. The NCO content of prepolymer was analyzed and found to be 2.0%. Warm prepolymer was mixed fast and mixture of 11.04 grams of triethylamine and 300 grams of water was added and mixed for 5 minutes to insure complete dispersion. No heating to flask was applied at this stage. Temperature in flask after adding of triethylamine and water was 48° C. Solution of 2.73 grams of ethylenediamine in 200 grams of water was added to dispersion and agitation was continued for 2 hours. The resulting dispersion was opalescent liquid which after drying produced film with following physical properties: Sword Hardness: 33; Tensile Strength: 4430 psi; Elongation at break: 180%; 100% modulus: 3418 psi; Tear resistance: 500 p/in.

Example 21

Preparation of Water-Borne Polyurethane Dispersion 45.04 grams of 80/20 grade toluene diisocyanate (TDI-80 from Loyondell Chemical Co.), 87.8 grams of polyether diol with molecular weight 1000 (Poly-G 20-112 from Arch Chemicals), 39.25 grams of methylethylketone was mixed and heated to 85° C. and maintained at that temperature for 1 hour. After 1 hour 28.0 grams of polyol with grafted carboxyl groups was added. This polyol with grafted carboxyl groups was obtained by reacting 1 mol of trimethylolpropane with 1 mol of succinic anhydride as described in Example 2 and had equivalent weight 124.33 for each OH group and equivalent weight 256.6 for each carboxyl group. After adding polyol with grafted carboxyl groups heating was continued for 1 more hour at 85° C. The NCO content of prepolymer was analyzed and found to be 2.35%. Warm prepolymer was mixed fast and mixture of 11.04 grams of triethylamine and 300 grams of water was added and mixed for 5 minutes to insure complete dispersion. No heating to flask was applied at this stage. Temperature in flask after adding of triethylamine and water was 49–50° C. Solution of 3.18 grams of ethylenediamine in 200 grams of water was added to dispersion and agitation was continued for 2 hours. The resulting dispersion was opalescent liquid which after drying produced film with following physical properties: Sword Hardness: 21; Tensile Strength: 3400 psi; Elongation at break: 370%; 100% modulus: 1200 psi; Tear resistance: 370 p/in.

Example 22

Preparation of Water-Borne Polyurethane Dispersion 72.5 grams of isophorone diisocyanate ("LUXATE IM" from Loyondell Chemical Co.), 60.3 grams of polyether diol with molecular weight 425 (Poly-G 20-265 made by Arch Chemicals), 0.0704 grams of dibutyltin dilaurate (Dabco T-12 from Air Products), 39.25 grams of methylethylketone was mixed and heated to 85° C. and maintained at that temperature for 1 hour. After 1 hour 28.0 grams of polyol with grafted carboxyl groups was added. This polyol with grafted carboxyl groups was obtained by reacting 1 mol of trimethylolpropane with 1 mol of succinic anhydride as described in Example 2 and had equivalent weight 129.11 for each OH group and equivalent weight 264.8 for each carboxyl group. After adding polyol with grafted carboxyl groups heating was continued for 1.5 more hours at 85° C. The NCO content of prepolymer was analyzed and found to be 3.0%. Warm prepolymer was mixed fast and mixture of 10.6 grams of triethylamine and 300 grams of water was added and mixed for 5 minutes to insure complete dispersion. No heating to flask was applied at this stage. Temperature in flask after adding of triethylamine and water was 45° C. Solution of 4.06 grams of ethylenediamine in 200 grams of water was added to dispersion and agitation was continued for 2 hours. The resulting dispersion was opalescent liquid which after drying produced film with following physical properties: Sword Hardness: 45; Tensile Strength: 5480 psi; Elongation at break: 8%; Sample was too brittle to perform tear resistance test.

Example 23

Preparation of Water-Borne Polyurethane Dispersion 72.5 grams of isophorone diisocyanate ("LUXATE IM" from Loyondell Chemical Co.), 60.3 grams of polyether diol with molecular weight 425 (Poly-G 20-265 from Arch Chemicals), 0.089 grams of dibutyltin dilaurate (Dabco T-12 from Air Products), 39.45 grams of methylethylketone was mixed and heated to 85° C. and maintained at that temperature for 1 hour. After 1 hour 28.0 grams of polyol with grafted carboxyl groups was added. This polyol with grafted carboxyl groups was obtained by reacting 1 mol of trimethylolpropane with 1 mol of succinic anhydride as described in Example 2 and had equivalent weight 129.11 for each OH group and equivalent weight 264.8 for each carboxyl group. After adding polyol with grafted carboxyl groups heating was continued for 1.5 more hours at 85° C. The NCO content of prepolymer was analyzed and found to be 3.0%. Warm prepolymer was mixed fast and mixture of 10.6 grams of triethylamine and 300 grams of water was added and mixed for 5 minutes to insure complete dispersion. No heating to flask was applied at this stage. Temperature in flask after adding of triethylamine and water was 45° C. Solution of 11.5 grams of isophorone diamine in 200 grams of water was added to dispersion and agitation was continued for 2 hours. The resulting dispersion was opalescent liquid which after drying produced film with following physical properties: Sword Hardness: 58; Sample was too brittle to perform tensile and tear resistance tests.

Example 24

Preparation of Water-Borne Polyurethane Dispersion 54.98 grams of isophorone diisocyanate ("LUXATE IM" from Loyondell Chemical Co.), 77.8 grams of polyether diol with molecular weight 1000 (Poly-G 20-112 from Arch Chemicals), 0.077 grams of dibutyltin dilaurate (Dabco T-12 from Air Products), 39.25 grams of methylethylketone was mixed and heated to 85° C. and maintained at that temperature for 1 hour. After 1 hour 28.0 grams of polyol with grafted carboxyl groups was added. This polyol with grafted carboxyl groups was obtained by reacting 1 mol of trimethylolpropane with 1 mol of succinic anhydride as described in Example 2 and had equivalent weight 124.33 for each OH group and equivalent weight 256.6 for each carboxyl group. After adding polyol with grafted carboxyl groups heating was continued for 1.5 more hours at 85° C. The NCO content of prepolymer was analyzed and found to be 2.4%. Warm prepolymer was mixed fast and mixture of 11.04 grams of triethylamine and 300 grams of water was added and mixed for 5 minutes to insure complete dispersion. No heating to flask was applied at this stage. Temperature in flask after adding of triethylamine and water was 49° C. Solution of 10.8 grams of isophorone diamine in 200 grams of water was added to dispersion and agitation was continued for 2 hours. The resulting dispersion was opalescent liquid which after drying produced film with following physical properties: Sword Hardness: 28; Tensile Strength: 4180 psi; Elongation at break: 330%; 100% modulus: 2090 psi; Tear resistance: 530 p/in.

Example 25

Preparation of Water-Borne Polyurethane Dispersion 54.98 grams of isophorone diisocyanate ("LUXATE IM" from Loyondell Chemical Co.), 77.8 grams of polyether diol with molecular weight 1000 (Poly-G 20-112 from Arch Chemicals), 0.080 grams of dibutyltin dilaurate (Dabco T-12 from Air Products), 39.25 grams of methylethylketone was mixed and heated to 85° C. and maintained at that temperature for 1 hour. After 1 hour 28.0 grams of polyol with grafted carboxyl groups was added. This polyol with grafted carboxyl groups was obtained by reacting 1 mol of trimethylolpropane with 1 mol of succinic anhydride as described in Example 2 and had equivalent weight 124.33 for each OH group and equivalent weight 256.6 for each carboxyl group. After adding polyol with grafted carboxyl groups heating was continued for 1.5 more hours at 85° C. The NCO content of prepolymer was analyzed and found to be 2.45%. Warm prepolymer was mixed fast and mixture of 11.04 grams of triethylamine and 300 grams of water was added and mixed for 5 minutes to insure complete dispersion. No heating to flask was applied at this stage. Temperature in flask after adding of triethylamine and water was 49–50° C. Solution of 8.23 grams of isophorone diamine in 200 grams of water was added to dispersion and agitation was continued for 2 hours. The resulting dispersion was opalescent liquid which after drying produced film with following physical properties: Sword Hardness: 24; Tensile Strength: 3730 psi; Elongation at break: 400%; 100% modulus: 1410 psi; Tear resistance: 290 p/in.

Example 26

Preparation of Water-Borne Polyurethane Dispersion 54.98 grams of isophorone diisocyanate ("LUXATE IM" from Loyondell Chemical Co.), 77.8 grams of polyether diol with molecular weight 1000 (Poly-G 20-112 from Arch Chemicals), 0.078 grams of dibutyltin dilaurate (Dabco T-12 from Air Products), 39.25 grams of methylethylketone was mixed and heated to 85° C. and maintained at that temperature for 1 hour. After 1 hour 28.0 grams of polyol with grafted carboxyl groups was added. This polyol with grafted carboxyl groups was obtained by reacting 1 mol of trimethylolpropane with 1 mol of succinic anhydride as described in Example 2 and had equivalent weight 124.33 for each OH group and equivalent weight 256.6 for each carboxyl group. After adding polyol with grafted carboxyl groups heating was continued for 1.5 more hours at 85° C. The NCO content of prepolymer was analyzed and found to be 2.3%. Warm prepolymer was mixed fast and mixture of 11.0 grams of triethylamine and 300 grams of water was added and mixed for 5 minutes to insure complete dispersion. No heating to flask was applied at this stage. Temperature in flask after adding of triethylamine and water was 49–50° C. Solution of 18.6 grams of isophorone diamine in 200 grams of water was added to dispersion and agitation was continued for 2 hours. The resulting dispersion was opalescent liquid which after drying produced film with following physical properties: Sword Hardness: 48; Tensile Strength: 4040 psi; Elongation at break: 225%; 100% modulus: 2777 psi; Tear resistance: 493 p/in.

Although the invention has been shown and described with respect to illustrative embodiments thereof, it should be appreciated that the foregoing and various other changes, omissions and additions in the form and detail thereof may be made without departing from the spirit and scope of the invention as delineated in the claims. All patents and patent applications mentioned are herein incorporated by reference in their entirety.

What is claimed is:

1. A carboxyl-containing monomer for use in preparing a polyurethane polymer, said carboxyl-containing monomer being the reaction product of a low molecular weight polyol compound selected from the group consisting of glycerol, trimethylolpropane, trimethylolethane, polyether polyols, and combinations thereof and an acid anhydride selected from the group consisting of maleic anhydride, phthalic anhydride, succinic anhydride, glutaric anhydride, and mixtures thereof, said reaction product being produced in the presence of 5–500 ppm phosphoric acid, said carboxyl-containing monomer having a viscosity in the range of about 3,000–100,000 centipoise, and having free oligomer content of less than 30 mg KOH/g.

2. The carboxy-containing monomer of claim 1, wherein said low molecular weight polyol compound is a polyether triol.

3. The carboxy-containing monomer of claim 1, wherein said carboxyl-containing monomer is made in the presence of 100–400 ppm phosphoric acid.

4. The carboxy-containing monomer of claim 3, wherein said carboxyl-containing monomer is made in the presence of 250–350 ppm phosphoric acid.

5. The carboxy-containing monomer of claim 1, wherein said viscosity of said carboxyl-containing monomer ranges from 3,000 to 50,000 cps.

6. The carboxy-containing monomer of claim 5, wherein said viscosity of said carboxyl-containing monomer ranges from 3,000 to 20,000 cps.

7. The carboxy-containing monomer of claim 1, wherein said free oligomer content of said carboxyl-containing monomer ranges from about 2 to 30 mg KOH/g.

8. The carboxy-containing monomer of claim 7, wherein said free oligomer content of said carboxyl-containing monomer ranges from about 2 to 20 mg KOH/g.

9. A method of preparing a carboxyl-containing monomer for use in preparation of a polyurethane polymer, comprising the step of combining a low molecular weight polyol compound selected from the group consisting of glycerol, trimethylolpropane, trimethylolethane, polyether polyols, and combinations thereof and an acid anhydride in the presence of 5–500 ppm phosphoric acid to produce said carboxyl-containing monomer, said carboxyl-containing monomer having a viscosity in the range of about 3,000 to about 100,000 cps and having a free oligomer content of less than about 30 mg KOH/g.

10. The method of claim 9, wherein said low molecular weight polyol compound is a polyether triol.

11. The method of claim 9, wherein said carboxyl-containing monomer is made in the presence of about 100 to 400 ppm phosphoric acid.

12. The method of claim 11, wherein said carboxyl-containing monomer is made in the presence of about 250–350 ppm phosphoric acid.

13. The method of claim 9, wherein said viscosity of said carboxyl-containing monomer ranges from about 3,000 to 50,000 cps.

14. The method of claim 13, wherein said viscosity of said carboxyl-containing monomer ranges from about 3,000 to 20,000 cps.

15. The method of claim 9, wherein said free oligomer content of said carboxyl-containing monomer ranges from about 2 to 30 mg KOH/g.

16. The method of claim 15, wherein said free oligomer content of said carboxyl-containing monomer ranges from about 2 to 20 mg KOH/g.

17. A prepolymer for use in preparing a polurethane polymer, said prepolymer being the reaction product of (1) the carboxyl-containing monomer of claim 1, and (2) a polyisocyanate compound selected from the group consisting of diisocyanate, 4,4'-dicyclohexylmethane diisocyanate, isophorone diisocyanate, 1,4'-tetramethylene diisocyanate, 1,10-decamethylene disiocyanate, 1,12-dodecamethylene diisocyanate, tolulene-2,4- or 2,6-diisocyanate, 1,5-naphthalene diisocyanates, 4-methoxy-1,3-phenylene diisocyanate, 4-chloro-1,3-phenylene diisocyanate, 2,4'-diisocyanatodiphenyl ether, 5,6-dimethyl-1,3-phenylate diisocyanate, 2,4-diemthyl-1,3-phenylene diisocyanate, 4,4'-diisocyanatodiphenylether, benzidene diisocyanate, 4,4'-diisocyanataodibenzyl, methylene-bis(4-phenylisocyanate), 1,3-phenylene diisocyanate, 4,4'-diphenylmethane diisocyanate, 2,4'-diphenylmethane diisocyanate, hexamethylene diisocyanate, 4,4'-dicyclohexylmethane diisocyanate, 1,12-dodecanediisocyanate, 2,4,4-trimethylhexamethylene diisocyanate, xylylene diisocyanate, tetramethyl-xylylene diisocyanate, polymethylene polyphenyl isocyanate, and combinations thereof, said prepolymer having a viscosity in the range of about 3,000 to about 100,000 cps.

18. A method of preparing a prepolymer for use in preparation of a polyurethane polymer, comprising the step of:

combining the prepolymer of claim 17 with a polyisocyanate compound selected from the group consisting of diisocyanate, 4,4'-dicyclohexylmethane diisocyanate, isophorone diisocyanate, 1,4'-tetramethylene diisocyanate, 1,10-decamethylene disiocyanate, 1,12-dodecamethylene diisocyanate, tolulene-2,4- or 2,6-diisocyanate, 1,5-naphthalene diisocyanates, 4-methoxy-1,3-phenylene diisocyanate, 4-chloro-1,3-phenylene diisocyanate, 2,4'-diisocyanatodiphenyl ether, 5,6-dimethyl-1,3-phenylate diisocyanate, 2,4-diemthyl-1,3-phenylene diisocyanate, 4,4'-diisocyanatodiphenylether, benzidene diisocyanate, 4,4'-diisocyanataodibenzyl, methylene-bis(4-phenylisocyanate), 1,3-phenylene diisocyanate, 4,4'-diphenylmethane diisocyanate, 2,4'-diphenylmethane diisocyanate, hexamethylene diisocyanate, 4,4'-dicyclohexylmethane diisocyanate, 1,12-dodecanediisocyanate, 2,4,4-trimethylhexamethylene diisocyanate, xylylene diisocyanate, tetramethyl-xylylene diisocyanate, polymethylene polyphenyl isocyanate, and combinations thereof, to produce said prepolymer, said prepolymer having a viscosity in the range of about 3,000 to about 100,000 cps.

19. A water-borne polyurethane polymer, said water-borne polyurethane polymer being the reaction product of (1) the prepolymer of claim 17, and (2) an amine compound selected from the group consisting of: triethylamine, tripropylamine, ethylene diamine, n-butylamine, diethylamine, trimethylamine, monoethanol amine, dimethylethanolamine, aminoalcohols, hydrazine, hexamethylene diamine, isophorone diamine, cyclohexane diamine, dimethylcyclohexylamine, tris(3-aminopropyl) amine, 2-methylpentamethylenediamine, 1,12-dodecanediamine, and combinations thereof.

* * * * *